(12) United States Patent
Sakai et al.

(10) Patent No.: US 8,679,568 B2
(45) Date of Patent: Mar. 25, 2014

(54) CITRULLINE-CONTAINING BEVERAGE

(75) Inventors: Yasushi Sakai, Tsukuba (JP); Takeshi Ikeda, Tsukuba (JP); Ayako Kamimura, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 12/743,172

(22) PCT Filed: Nov. 17, 2008

(86) PCT No.: PCT/JP2008/070842
§ 371 (c)(1),
(2), (4) Date: May 14, 2010

(87) PCT Pub. No.: WO2009/064004
PCT Pub. Date: May 22, 2009

(65) Prior Publication Data
US 2010/0255174 A1   Oct. 7, 2010

(30) Foreign Application Priority Data

Nov. 16, 2007  (JP) ................................. 2007-297950

(51) Int. Cl.
*B23K 20/233*   (2006.01)
(52) U.S. Cl.
USPC .......................................... 426/590; 426/656
(58) Field of Classification Search
None
See application file for complete search history.

(56) References Cited

U.S. PATENT DOCUMENTS

| | | | |
|---|---|---|---|
| 4,946,701 A * | 8/1990 | Tsai et al. | 426/597 |
| 5,411,757 A | 5/1995 | Buist et al. | |
| 7,897,192 B2 * | 3/2011 | Sherwood et al. | 426/583 |
| 2002/0136802 A1 * | 9/2002 | Mehansho et al. | 426/74 |
| 2003/0211133 A1 | 11/2003 | Meehan | |
| 2006/0147602 A1 * | 7/2006 | Sherwood et al. | 426/590 |
| 2007/0218150 A1 | 9/2007 | Akashi et al. | |
| 2007/0270355 A1 * | 11/2007 | Garcia et al. | 514/23 |
| 2009/0028967 A1 | 1/2009 | Sakurai | |

FOREIGN PATENT DOCUMENTS

| | | | | |
|---|---|---|---|---|
| JP | 62-083882 | A | 4/1987 | |
| JP | 63-049060 | A | 3/1988 | |
| JP | 05-246962 | A | 9/1993 | |
| JP | 2002-142677 | A | 5/2002 | |
| JP | 2004-173504 | A | 6/2004 | |
| JP | 2006-296379 | A | 11/2006 | |
| JP | 2007-039610 | A | 2/2007 | |
| JP | 2007-185113 | A | 7/2007 | |
| JP | 2007-274933 | A | 10/2007 | |
| JP | 2008-073007 | A | 4/2008 | |
| WO | WO 2005/105126 | A1 | 11/2005 | |
| WO | WO 2007080894 | A1 * | 7/2007 | ............ A23L 1/0528 |
| WO | WO 2008/105325 | A1 | 9/2008 | |

OTHER PUBLICATIONS

Kirin Beverage Products Line Up, List of Raw Materials and Nutrient Ingredients (Feb. 21, 2012) [as obtained on-line at URL: http://www.beverage.co.jp/csr/quality/ingredient.pdf on Jun. 27, 2013].
Nikkan Kogyo Shimbun, No. 133, p. 19 (Feb. 17, 2003).
Japanese Patent Office, Office Action in Japanese Patent Application No. 2009-541200 (Jul. 2, 2013).
Chengjin et al., *Beverage Industry*, 8(5): 13-16 and 24 (2005).
Chinese Patent Office, Notification of the Third Office Action in Chinese Patent Application No. 200880116481.5 (Apr. 12, 2013).

* cited by examiner

*Primary Examiner* — D. Lawrence Tarazano
*Assistant Examiner* — Tamra L Dicus
(74) *Attorney, Agent, or Firm* — Leydig, Voit & Mayer, Ltd.

(57) ABSTRACT

The invention provides an easy-to-drink beverage that contains citrulline, wherein the generation of bad odors due to storage or heating is suppressed. In particular, the invention provides a beverage that contains citrulline and citric acid, as well as sodium citrate or disodium hydrogen phosphate.

4 Claims, No Drawings

CITRULLINE-CONTAINING BEVERAGE

TECHNICAL FIELD

The present invention relates to a beverage containing citrulline and citric acid, as well as sodium citrate or disodium hydrogen phosphate.

BACKGROUND ART

Citrulline, not an amino acid that constitutes a protein in a living organism, is one of the intermediates in the urea cycle, and is produced from arginine along with nitrogen oxide (NO), which is known as a substance possessing vasodilating action, and is condensed with aspartic acid and regenerated into arginine. Citrulline is known to exhibit useful actions such as ammonia metabolism promotion (Non-patent Document 1), blood flow improvement by vasodilation (Non-patent Document 2), blood pressure reduction (Non-patent Document 3), neurotransmission (Non-patent Document 4), immunopotentiation (Non-patent Document 5), and active oxygen elimination (Patent Document 1). For this reason, with the expectation for these actions, it is common practice to take citrulline in the form of pharmaceuticals, functional foods and the like.

It is known that in aqueous solutions of basic amino acids such as lysine, arginine, ornithine, hydroxylysine, and histidine, bad odors are generated due to storage or heating, and that the bad odors are suppressed by adding a water-soluble reducing agent and a chelating agent to the aqueous solutions (Patent Document 2).

patent document 1: JP-A-2002-226370
patent document 2: JP-A-5-246962
non-patent document 1: Cell Biochemistry & Function, 2003, vol. 21, p. 85-91
non-patent document 2: European Journal of Pharmacology, 2001, vol. 431, p. 61-69
non-patent document 3: Journal of Clinical Investigation, 1991, vol. 88, p. 1559-1567
non-patent document 4: Gastroenterology, 1997, vol. 112, p. 1250-1259
non-patent document 5: The journal of biological chemistry, 1994, vol. 269, p. 9405-9408

DISCLOSURE OF THE INVENTION

Problems to Be Solved by the Invention

There is a demand for the development of an easy-to-drink beverage that contains citrulline, wherein the generation of bad odors due to storage or heating is suppressed.

Means for Solving the Problems

The present inventors extensively investigated to solve the above-described problems, found that by allowing citric acid and sodium citrate, or citric acid and disodium hydrogen phosphate, to be present in a beverage that contains citrulline, the generation of bad odors due to storage or heating is suppressed, and have developed the present invention.

Accordingly, the present invention relates to the following (1) to (5).
(1) A beverage containing citrulline and citric acid, as well as sodium citrate or disodium hydrogen phosphate.
(2) The beverage according to (1) above, wherein the citrulline concentration is 0.01 to 2% by weight.
(3) The beverage according to (1) or (2) above, wherein the blending ratio by weight of citric acid and sodium citrate is 5:1 to 1:6, and the combined concentration of citric acid and sodium citrate is 0.01 to 3% by weight.
(4) The beverage according to (1) or (2) above, wherein the blending ratio by weight of citric acid and disodium hydrogen phosphate is 3:1 to 1:5, and the combined concentration of citric acid and disodium hydrogen phosphate is 0.01 to 4% by weight.
(5) The beverage according to any of (1) to (4) above, wherein the pH is 2 to 7.

Advantages

According to the present invention, it is possible to provide an easy-to-drink beverage that contains citrulline, wherein the generation of bad odors due to storage or heating is suppressed.

BEST MODE FOR CARRYING OUT THE INVENTION

As the citrulline used in the present invention, L-citrulline and D-citrulline can be mentioned, with preference given to L-citrulline.

Citrulline can be acquired by a method based on chemical synthesis, a method based on fermentative production and the like. Citrulline can also be acquired by purchasing a commercially available product.

As an example of a method of chemically synthesizing citrulline, the method described in J. Biol. Chem. 122, 477 (1938), J. Org. Chem. 6, 410 (1941) can be mentioned.

As examples of methods of producing L-citrulline by fermentation, the methods described in JP-A-SHO-53-075387 and JP-A-SHO-63-068091 can be mentioned.

L-citrulline and D-citrulline can also be purchased from Sigma-Aldrich Corporation and the like.

In the present invention, a salt of citrulline may be used in place of citrulline.

As salts of citrulline, acid addition salts, metal salts, ammonium salts, organic amine addition salts, amino acid addition salts and the like can be mentioned.

As acid addition salts, inorganic acid salts such as hydrochlorides, sulfates, nitrates, and phosphates, and organic acid salts such as acetates, maleates, fumarates, citrates, malates, lactates, α-ketoglutarates, gluconates, caprylates, adipates, succinates, tartrates, and ascorbates can be mentioned.

As metal salts, alkali metal salts such as sodium salts and potassium salts, alkaline earth metal salts such as magnesium salts and calcium salts, aluminum salts, zinc salts and the like can be mentioned.

As ammonium salts, salts of ammonium, tetramethylammonium and the like can be mentioned.

As organic amine addition salts, salts of morpholine, piperidine and the like can be mentioned.

As amino acid addition salts, salts of glycine, phenylalanine, lysine, aspartic acid, glutamic acid and the like can be mentioned.

Of the above-described salts of citrulline, citrates and malates are preferably used; other salts, or 2 or more salts, may be used in combination as appropriate.

The beverage of the present invention can be produced by an ordinary method of beverage production except that citrulline and citric acid, as well as sodium citrate or disodium hydrogen phosphate, are contained.

The beverage of the present invention may be supplemented with saccharides, souring agents, preservatives such as antioxidants, colorants, flavoring agents, and other various additives for use in ordinary beverages. With the expectation for enhancement of health function, vitamins, minerals, and various functional ingredients may be added. Carbon dioxide may be pressed in to obtain a carbonated beverage.

The saccharides are not particularly limited, as far as they are usable for producing a beverage; any of monosaccharides, disaccharides, oligosaccharides, polysaccharides, sugar alcohols, and sweeteners is acceptable. As examples of the saccharides, glucose, fructose, sucrose, maltose, trehalose, xylitol, erythritol, reduced glucose syrup, dextrin, starch, sorbitol, maltitol, sucralose, aspartame, acesulfame K, stevia, saccharin sodium, dipotassium glycyrrhizinate, and thaumatin can be mentioned, with preference given to glucose, fructose, and sucrose.

The souring agents are not particularly limited, as far as they are usable for producing a beverage; examples include tartaric acid and malic acid.

The antioxidants are not particularly limited, as far as they are usable for beverages; examples include tocopherol, ascorbic acid, cysteine hydrochloride, and L-ascorbic acid stearic acid ester.

The colorants are not particularly limited, as far as they are usable for beverages; examples include Food Color Yellow No. 5, Food Color Red No. 2, Food Color Blue No. 2, carotenoid pigment, and tomato pigment.

The flavoring agents are not particularly limited, as far as they are usable for beverages; examples include lemon flavor, lemon-lime flavor, grapefruit flavor, and apple flavor.

The pH of the beverage of the present invention is normally 2 to 7, preferably 3 to 7, particularly preferably 3 to 6; the pH of the beverage is adjusted with pH regulators such as organic acids and inorganic acids.

The organic acids and inorganic acids are not particularly limited, as far as they are usable for producing a beverage. In place of organic acids and inorganic acids, salts thereof may be used. The salts of organic acids and inorganic acids are not particularly limited, as far as they are usable for producing a beverage.

The concentration of citrulline contained in the beverage of the present invention is normally 0.01 to 2% by weight, preferably 0.05 to 2% by weight, more preferably 0.1 to 2% by weight.

When sodium citrate is used in the beverage of the present invention, the blending ratio by weight of citric acid and sodium citrate contained in the beverage is normally 5:1 to 1:6, preferably 4:1 to 1:5, more preferably 3:1 to 1:4. The combined concentration of citric acid and sodium citrate is normally 0.01 to 3% by weight, preferably 0.05 to 2% by weight, more preferably 0.1 to 1% by weight. In the foregoing case, the citric acid ion concentration in the beverage is normally 0.0078 to 2.9% by weight, preferably 0.039 to 1.9% by weight, more preferably 0.078 to 0.95% by weight.

When disodium hydrogen phosphate is used in the beverage of the present invention, the blending ratio by weight of citric acid and disodium hydrogen phosphate contained in the beverage is normally 3:1 to 1:5, preferably 2:1 to 1:4, more preferably 1:1 to 1:3. The combined concentration of citric acid and disodium hydrogen phosphate is normally 0.01 to 4% by weight, preferably 0.05 to 3% by weight, more preferably 0.1 to 2% by weight.

In the present invention, when a citrulline citrate is used in place of citrulline, for example, the citric acid includes citric acid derived from a citrulline citrate.

By allowing citrulline, citric acid, sodium citrate or disodium hydrogen phosphate to be present in the beverage at the aforementioned concentrations, it is possible to provide an easy-to-drink beverage wherein the generation of bad odors due to storage or heating is suppressed.

Hereinafter, test examples are shown in which bad odor suppressing effects in the citrulline-containing beverage of the present invention were examined.

TEST EXAMPLE 1

Bad Odor Suppressing Effects of Citric Acid and Sodium Citrate

Each of the beverages of Examples 1 and 2 and Comparative Example 1 was placed in a covered bottle and heated at 120° C. for 20 minutes, after which a sensory evaluation test was performed by six subjects. Ratings were made in comparison with the bad odor produced in Comparative Example 1, using the evaluation criteria: 1; effective in deodorization, 2; slightly effective in deodorization, 3; little effective in deodorization, 4; ineffective in deodorization. The results are shown in Table 1.

TABLE 1

| Mean value of evaluation | |
| --- | --- |
| Example 1 | 1.8 |
| Example 2 | 1.3 |

From Table 1, it is evident that with the beverages of Examples 1 and 2, which contained citric acid and sodium citrate, a definite deodorant effect was obtained.

TEST EXAMPLE 2

Bad Odor Suppressing Effects of Citric Acid and Disodium Hydrogen Phosphate

Each of the beverages of Examples 3 and 4 and Comparative Example 1 was placed in a covered bottle and heated at 120° C. for 20 minutes, after which a sensory evaluation test was performed by five subjects. Ratings were made in comparison with the bad odor produced in Comparative Example 1 using the evaluation criteria: 1; effective in deodorization, 2; slightly effective in deodorization, 3; little effective in deodorization, 4; ineffective in deodorization. The results are shown in Table 2.

TABLE 2

| Mean value of evaluation | |
| --- | --- |
| Example 3 | 1.5 |
| Example 4 | 1.4 |

From Table 2, it is evident that with the beverages of Examples 3 and 4, which contained citric acid and disodium hydrogen phosphate, a definite deodorant effect was obtained.

Hereinafter, examples of the present invention are shown.

Example 1

Citrulline-Containing Beverage (1)

Ingredient Amount (g)

| | |
|---|---|
| L-citrulline (manufactured by Kyowa Hakko Kogyo) | 1.00 |
| Citric acid (manufactured by Kishida Chemical) | 0.75 |
| Sodium citrate (manufactured by Kishida Chemical) | 0.25 |

These ingredients were dissolved in ultrapure water to make a total volume of 100 ml.

Example 2

Citrulline-Containing Beverage (2)
Ingredient Amount (g)

| | |
|---|---|
| L-citrulline (manufactured by Kyowa Hakko Kogyo) | 1.00 |
| Citric acid (manufactured by Kishida Chemical) | 0.20 |
| Sodium citrate (manufactured by Kishida Chemical) | 0.80 |

These ingredients were dissolved in ultrapure water to make a total volume of 100 ml.

Example 3

Citrulline-Containing Beverage (3)
Ingredient Amount (g)

| | |
|---|---|
| L-citrulline (manufactured by Kyowa Hakko Kogyo) | 1.00 |
| Citric acid (manufactured by Kishida Chemical) | 1.00 |
| Disodium hydrogen phosphate (manufactured by Wako Pure Chemical Industries) | 1.00 |

These ingredients were dissolved in ultrapure water to make a total volume of 100 ml.

Example 4

Citrulline-Containing Beverage (4)
Ingredient Amount (g)

| | |
|---|---|
| L-citrulline (manufactured by Kyowa Hakko Kogyo) | 1.00 |
| Citric acid (manufactured by Kishida Chemical) | 0.50 |
| Disodium hydrogen phosphate (manufactured by Wako Pure Chemical Industries) | 1.50 |

These ingredients were dissolved in ultrapure water to make a total volume of 100 ml.

COMPARATIVE EXAMPLE 1

A beverage containing 1% by weight of L-citrulline in ultrapure water was prepared.

INDUSTRIAL APPLICABILITY

According to the present invention, it is possible to provide an easy-to-drink beverage that contains citrulline, wherein the generation of bad odors due to storage or heating is suppressed.

The invention claimed is:

1. A beverage consisting of (a) 0.01-1.0% by weight citrulline, (b) citric acid, (c) disodium hydrogen phosphate, (d) water, and (e) one or more supplements selected from saccharides, souring agents, preservatives, colorants, flavoring agents, functional ingredients, and carbon dioxide,
wherein
the saccharides are selected from glucose, fructose, sucrose, maltose, trehalose, xylitol, erythritol, reduced glucose syrup, dextrin, starch, sorbitol, maltitol, sucralose, aspartame, acesulfame K, stevia, saccharin sodium, dipotassium glycyrrhizinate, and thaumatin,
the blending ratio by weight of citric acid and disodium hydrogen phosphate is 1:1 to 1:3, and
the combined concentration of citric acid and disodium hydrogen phosphate is 0.01-2% by weight.

2. The beverage according to claim 1, wherein the pH is 2 to 7.

3. The beverage of claim 1, wherein the beverage contains one or more functional ingredients selected from the group consisting of vitamins and minerals.

4. The beverage according to claim 3, wherein the pH is 2 to 7.

* * * * *